United States Patent [19]

Kutny et al.

[11] Patent Number: 5,041,233
[45] Date of Patent: Aug. 20, 1991

[54] PROCESS FOR PREPARING SOAP-ACYL ISETHIONATE COMPOSITIONS

[75] Inventors: Yuriy O. Kutny, Rutherford; Frederick S. Osmer, Parsippany, both of N.J.; Joseph J. Podgorsky, Slate Hill, N.Y.; David A. Richardson, Portage, Ind.; Karla J. Rys, Little Ferry, N.J.

[73] Assignee: Lever Brothers Company, Division of Conopco, Inc., New York, N.Y.

[21] Appl. No.: 535,244

[22] Filed: Sep. 8, 1990

Related U.S. Application Data

[63] Continuation-in-part of Ser. No. 325,602, Mar. 20, 1989, abandoned, which is a continuation-in-part of Ser. No. 189,940, May 3, 1988, abandoned.

[51] Int. Cl.$^5$ .......................... C11D 9/32; C11D 13/10
[52] U.S. Cl. ..................................... 252/121; 252/132; 252/134; 252/DIG. 16
[58] Field of Search ........ 252/121, 132, 134, DIG. 16

[56] References Cited

U.S. PATENT DOCUMENTS

| | | | |
|---|---|---|---|
| 2,578,366 | 2/1945 | Mills | 252/367 |
| 3,657,146 | 4/1972 | Framson et al. | 252/369 |
| 4,260,507 | 4/1981 | Barrett | 252/121 |
| 4,474,683 | 10/1984 | Story et al. | 252/369 |
| 4,479,884 | 10/1984 | Clarke et al. | 252/132 |
| 4,663,070 | 5/1987 | Dobrovolny et al. | 252/121 |
| 4,695,395 | 9/1987 | Caswell et al. | 252/121 |
| 4,707,288 | 11/1987 | Irlam et al. | 252/121 |
| 4,820,447 | 4/1989 | Medcalf et al. | 252/117 |

Primary Examiner—Paul Lieberman
Assistant Examiner—Alexander G. Ghyka
Attorney, Agent, or Firm—Milton L. Honig

[57] ABSTRACT

A batch and continuous process is disclosed for the production of a composition comprising alkali metal salts of $C_8$–$C_{22}$ alkyl fatty monocarboxylic acid and $C_8$–$C_{22}$ acyl isethionate in a ratio of 20:1 to 1:0.98. Both batch and continuous routes require that the saponifying aqueous caustic solution includes sodium hydroxide and sodium isethionate maintained as a hot solution at a temperature of from 180° F. to about 200° F. For the batch route, the sequence of steps require the caustic solution to be added slowly to the fatty acid. In the continuous process, it is advantageous to introduce fatty acid upstream from the point where the caustic solution stream enters the mixing chamber.

33 Claims, 2 Drawing Sheets

PROCESS FOR PREPARING SOAP-ACYL ISETHIONATE COMPOSITIONS

This is a continuation-in-part application of Ser. No. 325,602, filed Mar. 20, 1989, now abandoned, which is a continuation-in-part of Ser. No. 189,940 filed May 3, 1988, now abandoned.

BACKGROUND OF THE INVENTION

1. Field of the Invention

The invention relates to a process for preparing compositions comprising a major amount of soap and a minor amount of acyl isethionate.

2 The Prior Art

Soap is an excellent cleaning agent but is quite harsh to the skin. A study by Frosh & Kligman, J. Amer. Acaderm. pp. 35 (1979), revealed that substantial replacement of soap with an alternative detergent such as an acyl fatty isethionate would provide a more skin compatible system. Unfortunately, this alternative is expensive. Less costly solutions are needed to provide the consumer with an economical, yet mild, product.

One approach to resolving the problem has been reported in U.S. Pat. No. 4,695,395 (Caswell et al.). The patent reports that bars containing a major amount of soap and a minor amount of acyl isethionate can be rendered relatively non-irritating by incorporation of non-acylated sodium isethionate. On the heels of this discovery, there was presented a need for a process to prepare such compositions.

U.S. Pat. No. 4,663,070 (Dobrovolny et al.) discloses a batch process wherein a reactor containing a major amount of soap, a minor amount of $C_{10}$–$C_{16}$ acyl isethionate, sodium isethionate, water, stearic acid, sodium chloride and certain minor additives are heated at 210°–218° F. under agitation. The reaction was judged as complete and terminated when the blend had passed a second peak in viscosity.

A related case, U.S. Pat. No. 4,707,288 (Irlam et al.) reports an essentially identical formulation prepared in a reactor under conditions of shear maintaining a temperature of from 60° C. to about 90° C. Thereafter, the composition is feed to a plodder and extruded to form a detergent bar.

Each of the foregoing processes begin with soap as a starting material. A necessary condition for the soap/acyl isethionate based mixing is the need for certain initial levels of water. Without a minimum water level in the raw materials, blending would be difficult and gritty product would result. A disadvantage of the aforementioned processes containing water is that moisture must be reduced through evaporation to arrive at an acceptable end product. There is a critical window of moisture beyond which bar physical properties are adversely affected. A second problem with the aforementioned processes is the time required in blending soap with acyl isethionate before there can be achieved the appropriate product viscosity.

Elimination of a drying step has long been known in the soap making art. For instance, U.S. Pat. No. 2,578,366 (Mills) meters an aqueous sodium hydroxide stream and a fatty acid slurry stream into a mixing reactor. Typically, the aqueous solution of caustic soda is maintained at about 80°–95° F. Temperatures for the neutralization and subsequent soap mixing range from about 130° to 215° F.

Along similar lines, U.S. Pat. No. 3,657,146 (Framson et al.) reveals a method for the direct production of soap from fatty acid under reaction temperatures of 120°–180° C. Separate streams of tallow/coconut (80/20) fatty acids, of stoichiometric amounts aqueous sodium hydroxide, and of sodium chloride are pumped into a reactor vessel.

In principle, it would appear attractive to form soap in situ, neutralizing fatty acid, while simultaneously feeding acyl isethionate into the blend. However, there is a problem. Acyl isethionate is susceptible to hydrolysis. Thus, before such a route were to be feasible, ways had to be found to reduce the hydrolysis threat.

Accordingly, it is an object of the present invention to provide a process for preparing toilet bars containing a major amount of soap and a minor amount of acyl isethionate.

A further object of this invention is to provide a method for producing a soap/acyl isethionate bar which substantially eliminates the need for drying and thereby increases production rates.

A still further object of this invention is to provide a process for preparing soap/acyl isethionate compositions by a route which minimizes hydrolysis of the acyl isethionate component.

Another object of the present invention is to provide a process yielding a soap/acyl isethionate composition having consumer use and toilet bar processing properties that fall within commercially acceptable parameters.

These and other objects of the present invention will become apparent as further details are provided in the subsequent discussion and Examples.

SUMMARY OF THE INVENTION

A process is provided for the production of a composition comprising alkali metal salts of $C_8$–$C_{22}$ alkyl fatty monocarboxylic acid and $C_8$–$C_{22}$ acyl isethionate in a ratio of 20:1 to 1:0.98, said process comprising the steps of:

(i) forming an aqueous caustic solution comprising sodium hydroxide and alkali metal isethionate, said solution maintained at a temperature from at least 180° F. to about 200° F. to obtain a hot solution;

(ii) charging $C_8$–$C_{22}$ alkyl fatty monocarboxylic acid to a reactor and maintaining said fatty monocarboxylic acid at an elevated temperature under high speed mixing;

(iii) slowly adding said hot caustic solution to said fatty monocarboxylic acid in said reactor; and (iv) feeding said acyl isethionate salt to said reactor at a time either prior to the addition of said caustic solution in step (ii) or subsequent to step (iii).

There is also provided a process for continuous production of a composition comprising alkali metal salts of $C_8$–$C_{22}$ alkyl fatty acid and $C_8$–$C_{22}$ acyl isethionate in a ratio of about 20:1 to 1:0.98, said process comprising the steps of:

(i) forming an aqueous caustic solution comprising sodium hydroxide and alkali metal isethionate, said solution maintained at a temperature of at least 180° F. to about 200° F. to obtain a hot solution;

(ii) separately and simultaneously charging a first feed stream of said $C_8$–$C_{22}$ alkyl fatty monocarboxylic acid and a second feed stream of said hot caustic solution into a mixing chamber to form said alkali metal $C_8$–$C_{22}$ alkyl fatty monocarboxylic acid salt; and (iii) mixing said formed alkali metal $C_8$-$C_{22}$ alkyl fatty monocarboxylic acid salt with said alkali metal $C_8$-$C_{22}$ acyl isethionate salt to form said composition, and wherein said acyl isethionate salt is introduced to said mixing chamber as a slurry in said fatty monocarboxylic acid or introduced subsequent to step (ii).

BRIEF DESCRIPTION OF THE DRAWING

The process of the invention will now be described with reference to the accompanying drawings. These are as follows.

DETAILED DESCRIPTION OF THE INVENTION

Both a batch and continuous method for the production of soap/acyl isethionate compositions is herein reported which utilizes fatty acids as a starting material for the soap. Unless otherwise stated, parameters found for the batch route are equally relevant to that of the continuous one.

Broadly, the batch process involves mixing together acyl isethionate and distilled fatty acids to produce a slurry in a reactor vessel. The reactor vessel is maintained at a temperature from 180° to 300° F. Under agitation, the fatty acids in the slurry are neutralized by slow addition to the vessel of a hot caustic solution comprising sodium hydroxide, sodium isethionate and water. The amount of sodium hydroxide in the caustic solution will range from 5 to 80%, preferably 20 to 80% by weight, and the amount of sodium isethionate in the caustic solution will range from 0 to 20%, preferably from 0.5 to 10%, optimally from 2 to 5% by weight of the solution. After a mixing period, e.g. about 30 minutes, the resultant blend is discharged from the vessel for further processing including cooling on chill rolls, milling, plodding and stamping operations.

A factor of critical importance in obtaining a composition that minimizes the hydrolysis of the acyl isethionate concerns that of the caustic solution temperature. The temperature of this solution must be maintained at 180° F. to about 200° F., preferably about 200° F. Temperatures less than 180° F. result in a substantial crystallization of caustic and increased acyl isethionate hydrolysis.

Other parameters also have an effect upon acyl isethionate hydrolysis. Best yields are obtained where there is sufficient electrolyte present in the caustic solution to achieve a saturated state. Typical electrolytes are alkali metal and alkaline earth chloride and sulfate salts, especially sodium chloride. Amounts of electrolyte that will normally achieve the saturation level will range from about 0.4 to about 2%, preferably from about 0.4% to about 1.5%, optimally about 0.8% based on the weight of the final product composition.

It has also been found desirable that there be slow addition, accompanied by a high rpm mixing, of caustic solution to the fatty acid/acyl isethionate components.

Certain criticalities beyond those mentioned above are necessary for the continuous process. A feed of fatty acid should be injected into a reactor upstream from where the caustic solution enters. An extruder is a quite suitable reactor vessel for this purpose. Fatty acids are normally held in their feed vessel at about 200° F. and thus are fed in the molten state to the extruder. Acyl isethionate may be introduced in combination with the molten fatty acid. Alternatively, acyl isethionate may be introduced into the reactor at a point downstream from where the caustic solution enters. Further ingredients such as stearic acid should be dosed to the reactor at a point downstream from the aqueous caustic entry point.

EXAMPLE 1

BATCH PROCESS

Figure 1:
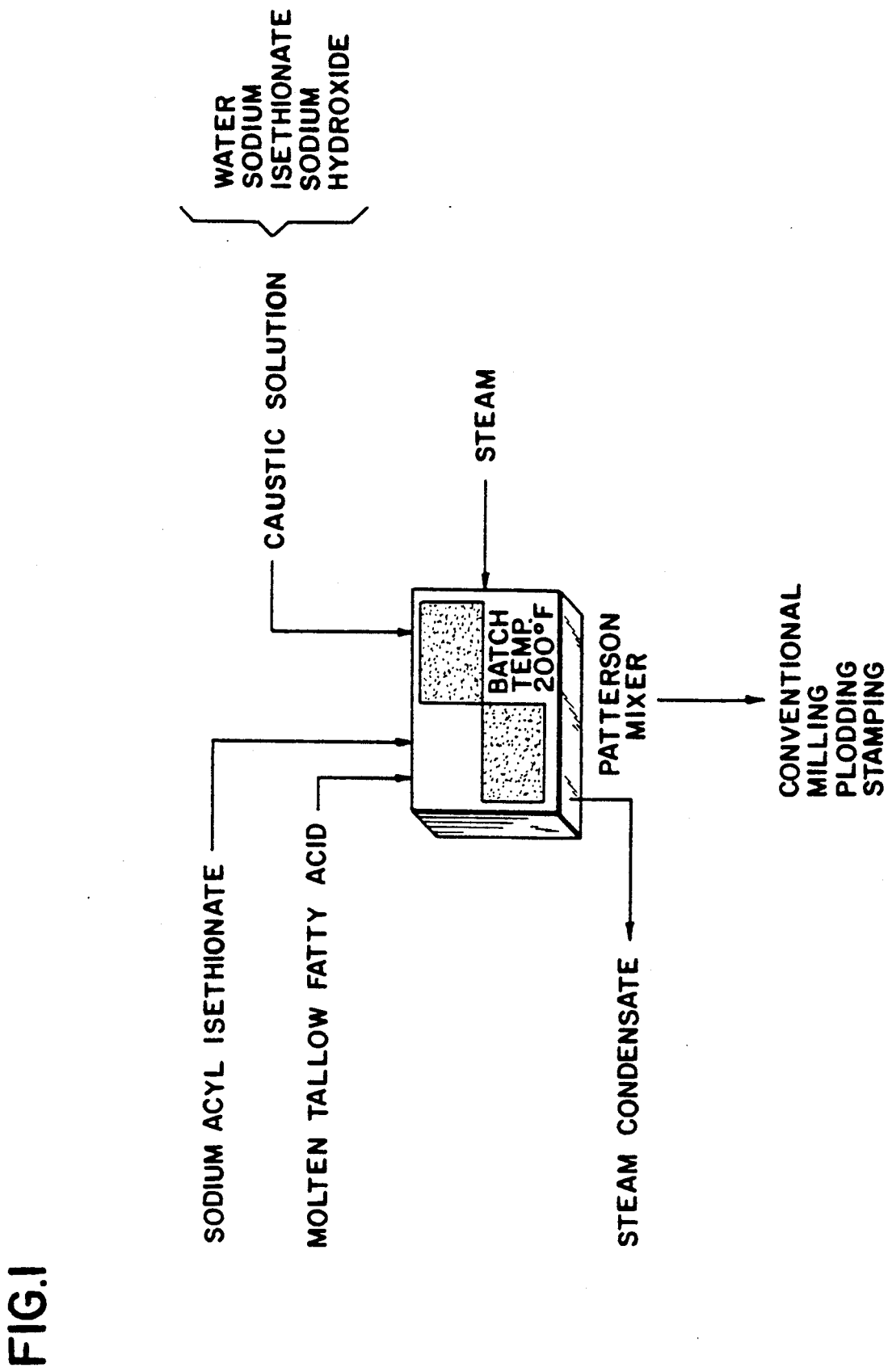
FIG. 1 is a schematic flow diagram for a batch process.

A flow diagram of the batch process is schematically illustrated in FIG. 1. Processing commences with molten tallow fatty acid and cocoyl isethionate being charged into a Patterson mixer. These two ingredients are mixed and heated for no longer than 10 minutes. Mixing and heating produces an off-white suspension or slurry of cocoyl isethionate/tallow fatty acid.

Neutralization of the fatty acids was conducted at about 200° F. Upon achieving this temperature, a caustic solution of sodium hydroxide, sodium isethionate and water was metered by peristaltic pump into the Patterson mixer containing the cocoyl isethionate/tallow fatty acid batch. Addition was performed at a rate such that the caustic solution was completely added within 4 to 5 minutes. During the latter part of this time interval, normally around the 4.5 minute mark, batch viscosity increased to the point where it became semi-solid. Phase transition of material in the reactor was accompanied by a substantial energy release. A brief temperature spike of around 20° F. occurred but temperature returned to the set point within 3-5 minutes.

Upon addition of the caustic solution, the batch was mixed at 200° F. for at least 30 minutes. Stearic acid was then added and mixing continued for an additional 5 minutes. Thereafter, the product was removed from the reactor and chill rolled into ribbons. Perfume, preservatives and other minor ingredients were surface coated onto the ribbons. Further processing included conventional milling, plodding and stamping to obtain final bars. The finished, saponified formulation is outlined in Table I.

TABLE I

| Theoretical Final Composition (before hydrolysis) | |
|---|---|
| Ingredient | Weight % |
| Sodium fatty monocarboxylic acid salt (82/18 tallow/coconut soap) | 51.17 |
| Sodium cocoyl isethionate | 21.93 |
| Stearic/palmitic acid | 6.19 |
| Coconut fatty acid | 1.33 |
| Sodium isethionate | 5.00 |
| Water | 10.50 |
| Fragrance | 1.50 |
| Titanium dioxide | 1.00 |
| Sodium chloride | 0.43 |
| Miscellaneous minor ingredients | 0.22 |

EXAMPLE 2

The effects of temperature were evaluated in a series of experiments outlined in Table II. Process and composition were essentially identical to that described in Example 1.

TABLE II

Percent Cocoyl Isethionate Loss by Varying Caustic Solution Temperature

| Experiment No. | Electrolyte (Sodium Chloride) (% Wt/Wt Product) | Caustic Solution Temperature (°F.) | % Cocoyl Isethionate Active Loss |
| --- | --- | --- | --- |
| 1 | 0 | 200 | 5.4 |
| 2 | 0 | 150 | 24.1 |
| 3 | 0.43 | 200 | 3.8 |
| 4 | 0.43 | 160 | 15.6 |
| 5 | 0.86 | 200 | 2.8 |
| 6 | 0.86 | 150 | 12.2 |

From the Table, it is seen that the caustic solution temperature is the major criticality that effects the hydrolysis (loss) of cocoyl isethionate. Experiments 1, 3 and 5 exhibit active loss of 5.4% or less. By contrast, at 150°–160° F. the loss is more than tripled falling within the range 12.2 to 24.1%. See Experiments 2, 4 and 6.

EXAMPLE 3

Electrolyte level also has some effect upon limiting the amount of cocoyl isethionate lost through hydrolysis. Table III sets forth relationship of electrolyte to that of % cocoyl isethionate loss.

TABLE III

% Cocoyl Isethionate Loss by Varying Electrolyte Concentration

| Experiment No. | Initial Batch Moisture (%) | Electrolyte (Sodium Chloride) (% Wt/Wt Product) | Caustic Solution Temperature (°F.) | % Cocoyl Isethionate Active Loss* |
| --- | --- | --- | --- | --- |
| 7a | 14 | 0 | Ambient | 11.53 |
| 8a | 14 | 0.43 | Ambient | 10.74 |
| 9a | 14 | 0.86 | Ambient | 9.60 |
| 10a | 14 | 0.97 | Ambient | 9.65 |
| 11a | 14 | 1.08 | Ambient | 8.96 |
| 12a | 14 | 1.3 | Ambient | 8.98 |
| 7b | 18 | 0 | Ambient | 11.63 |
| 8b | 18 | 0.43 | Ambient | 10.61 |
| 9b | 18 | 0.86 | Ambient | 9.79 |
| 10b | 18 | 0.97 | Ambient | 9.01 |
| 11b | 18 | 1.08 | Ambient | 8.97 |
| 12b | 18 | 1.3 | Ambient | 9.29 |
| 13 | 18 | 0 | Ambient | 11.78 |
| 14 | 18 | 0 | 200 | 8.82 |
| 15 | 18 | 1.3 | 200 | 3.86 |

*Note: Experiments No. 7b–12b are the average of at least 2 runs.

From Table III, it is evident that Active hydrolysis is slowed in the presence of certain amounts of salt. Yield improvement occurs up to a level of about 1.3%. Beyond levels of 2% electrolyte, other physical properties become evident such as that of unacceptable mush values. A combination of a 1.3% salt level with a caustic temperature of 200° F. was particularly effective in experiment No. 15 where only 3.86% hydrolysis occurred.

TABLE IV

% Cocoyl Isethionate Loss by Varying the Type of Electrolyte

| Experiment No. | Electrolyte | Electrolyte Concentration (% Wt/Wt Product) | % Cocoyl Isethionate Active Loss |
| --- | --- | --- | --- |
| 16 | Potassium chloride | 0.86 | 8.93 |
| 17 | Calcium chloride | 0.86 | 8.98 |
| 18 | Lithium chloride | 0.86 | 9.29 |
| 19 | Calcium sulfate | 0.86 | 8.98 |

From Table IV, it is evident that the particular type of electrolyte is not critical. Any inorganic salt that readily dissolves in the caustic solution will be acceptable.

EXAMPLE 4

Figure 2:
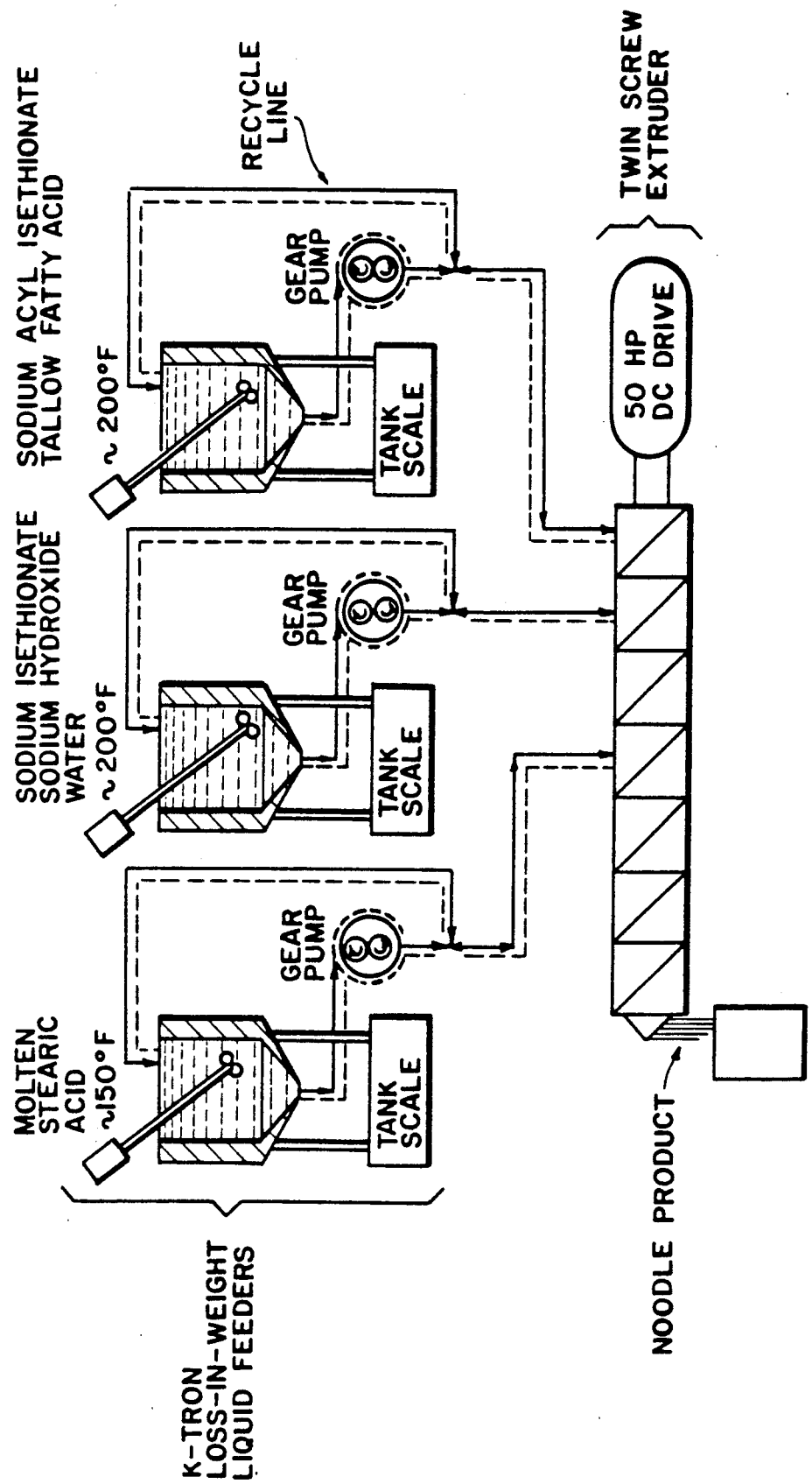
FIG. 2 is a schematic flow diagram for a continuous process utilizing an extruder a reactor.

This Example illustrates the continuous process outlined schematically in FIG. 2. The Figure shows two liquid streams being fed to a twin screw extruder. More particularly, the extruder was a Werner and Pfleiderer Corporation 32L/D twin screw extruder having a 40 mm screw flight diameter. The first feed stream is a slurry of cocoyl isethionate/tallow fatty acid. Downstream therefrom is introduced a second feed stream of caustic solution comprising sodium hydroxide, sodium isethionate and water. Screw configuration of the extruder is such that caustic and fatty acid streams are rapidly completely neutralized and continue mixing as they travel to exit the apparatus. Residence times within the extruder normally ranged from 3 to 5 minutes, depending upon product throughput, screw rpm and configuration.

The cocoyl isethionate/tallow fatty acid feed stream was prepared using a Schold intensive mixer. This stream was prepared by first adding molten tallow fatty acid to the mixer with agitation. After reaching a temperature of 200° F., cocoyl isethionate was added to the molten tallow fatty acid. Heating at 200° F. with mixing was continued for 20 minutes whereafter the mixture was transferred to a waiting extruder feed tank.

Caustic solution was prepared by mixing water, 50 weight % sodium hydroxide, and 56 weight % sodium isethionate together in a feed tank. It was found necessary that the water be added first to the mixed tank to provide sufficient solvent for the two solutes (sodium hydroxide and sodium isethionate) to avoid precipitation of the sodium hydroxide.

The extruder had a barrel whose length was divided into five 5/1 L/D sections that were controlled with separate dual output, self tuning controllers. These controllers regulated electrical heating or closed loop cooling of the respective barrel sections. Feed rates to the extruder were controlled via a K-tron loss-in-weight liquid feed system. Each feed tank rested on top of a scale which relayed tank weight information to a controller. Changes in tank weight with time were monitored by the controller. The controller then regulated the rpm of a gear pump feeding the extruder. The system automatically compensated for a decreasing suction head occurring as a result of the liquid height in the feed tank decreasing as feeding progressed. At an entrance to the extruder, each feed line was fitted with an injection nozzle allowing feed to enter into the extruder under a specified pressure.

Upon start up, the caustic line was first opened and then the cocoyl isethionate/tallow fatty acid feed line opened thereafter. Extruder screw rpm was set at 400 to 500 rpm. Feed line injection pressures were adjusted to 50 psi. Feed controllers were normally set to achieve a product throughput of 200 pounds/hour.

With the above-identified equipment, a series of continuous runs were conducted. Table V lists details of these experiments. The continuous process achieved a cocoyl isethionate loss of only 8–10 weight %. These results are significant considering that in batch experiments where a total caustic charge is added in a single shot, cocoyl isethionate hydrolysis is in the area of 20–30%, and sandy bars result.

TABLE V

| Continuous Extruder Processing | | | |
|---|---|---|---|
| Neutralization Moisture (%) | Neutralization Temperature (°F.) | Sample No. | % Cocoyl Isethionate Loss |
| 16.36 | 80 | 1 | 3.55 |
|  | 100 | 2 | 5.41 |
|  | 120 | 3 | 7.74 |
| 14.98 | 80 | 1 | 8.03 |
|  | 100 | 2 | 8.80 |
|  | 120 | 3 | 9.70 |
| 14.98 | 80 | 1 | 9.86 |
|  | 100 | 2 | 8.28 |
|  | 120 | 3 | 8.59 |
| 15.01 | 80 | 1 | 9.82 |
|  | 100 | 2 | 7.25 |
|  | 120 | 3 | 9.03 |
| 18.00 | 80 | 1 | 9.87 |
|  | 100 | 2 | 9.50 |
|  | 120 | 3 | 10.22 |

EXAMPLE 5

The following experiment was run similar to that described in Example 1 except that the caustic solution was added to the batch reactor concurrently with cocoyl isethionate/tallow fatty acid. Table VI summarizes the parameters of these experiments.

TABLE VI

| Batch Process with Simultaneous Addition of All Reactants | | | | | | | |
|---|---|---|---|---|---|---|---|
| Experiment No. | Processing Temperature (°F.) | % Water in Batch After Neutralization is Complete | Caustic Solution Composition | | | Final % Cocoyl Isethionate | % Cocoyl Isethionate Loss* |
| | | | % Water | % Sodium Hydroxide | % Sodium Isethionate | | |
| 20 | 180 | 14.2 | 56.3 | 39.8 | 3.9 | 17.75 | 22.8 |
| 21 | 200 | 14.2 | 56.3 | 39.8 | 3.9 | 16.55 | 28.2 |
| 22 | 180 | 18.0 | 65.3 | 31.6 | 3.1 | 16.45 | 26.4 |
| 23 | 200 | 18.0 | 65.3 | 31.6 | 3.1 | 15.9 | 33.2 |

Note
*Average of two runs.

From Table VI, it is evident that by the concurrent addition of caustic solution with the other reactants, the amount of cocoyl isethionate loss is quite significant, ranging from 22.8 to 33.2.

TABLE VII

| Batch Process Studying Effects of Cocoyl Isethionate Point of Addition | | |
|---|---|---|
| Experiment No. | Isethionate Addition Method | % Cocoyl Isethionate Loss* |
| 24 | Control | 23.0 |
| 25 | Modified | 9.9 |
| 26 | Reverse | 3.7 |

*Control = cocoyl isethionate/tallow fatty acid added prior to caustic addition.
Modified = tallow fatty acid followed by slight excess caustic addition (to neutralize the coco fatty acid impurity in cocoyl isethionate) and cocoyl isethionate added last after soap formation.
Reverse = tallow fatty acid followed by equivalent weight caustic addition and cocoyl isethionate added last after soap formation.

Evident from Table VII is that with respect to the batch process, the preferred method is that of reverse addition. Therein, the least amount of cocoyl isethionate is lost.

The foregoing description and examples illustrate selected embodiments of the present invention and in light thereof various modifications will be suggested to one skilled in the art, all of which are in the spirit and purview of this invention.

What is claimed is:

1. A process of the production of a composition comprising alkali metal salts of $C_8$–$C_{22}$ alkyl fatty monocarboxylic acid and $C_8$–$C_{22}$ acyl isethionate in a ratio of 20:1 to 1:0.98, said process comprising the steps of:
   (i) forming an aqueous caustic solution comprising sodium hydroxide in an amount sufficient to neutralize a $C_8$–$C_{22}$ alkyl fatty monocarboxylic acid and from 0 to 20% by weight of an alkali metal isethionate, said solution being maintained at a temperature from at least 180° F. to about 200° F. to obtain a hot solution;
   (ii) charging said $C_8$–$C_{22}$ alkyl fatty monocarboxylic acid to a reactor and agitating said fatty monocarboxylic acid under high speed mixing;
   (iii) feeding said acyl isethionate salt to said reactor; and
   (iv) slowly adding said hot caustic solution to said fatty monocarboxylic acid in said reactor.

2. A process according to claim 1 wherein the caustic solution is maintained at a temperature of about 200° F.

3. A process according to claim 1 wherein the acyl isethionate salt is added to the reactor together in admixture with said fatty monocarboxylic acid.

4. A process according to claim 1 wherein the aqueous caustic solution contains from about 0.4 to about 2% of an electrolyte.

5. A process according to claim 1 wherein the aqueous caustic solution contains from about 0.8 to about 1.5% of an electrolyte.

6. A process for continuous production of a composition comprising alkali metal salts of $C_8$–$C_{22}$ alkyl fatty acid and $C_8$–$C_{22}$ acyl isethionate in a ratio of about 20:1 to 1:0.98, said process comprising the steps of:
  (i) forming an aqueous caustic solution comprising sodium hydroxide in an amount sufficient to neutralize a $C_8$–$C_{22}$ alkyl fatty monocarboxylic acid and from 0 to 20% by weight of an alkali metal isethionate, said solution being maintained at a temperature from at least 180° F. to about 200° F. to obtain a hot solution;
  (ii) separately and simultaneously charging a first feed stream of said $C_8$–$C_{22}$ alkyl fatty monocarboxylic acid and a second feed stream of said hot caustic solution into a mixing chamber to form said alkali metal $C_8$–$C_{22}$ alkyl fatty monocarboxylic acid salt; and
  (iii) mixing said formed alkali metal $C_8$–$C_{22}$ alkyl fatty monocarboxylic acid salt with said alkali metal $C_8$–$C_{22}$ acyl isethionate salt to form said composition, and wherein said acyl isethionate salt is introduced to said mixing chamber as a slurry in said fatty monocarboxylic acid.

7. A process according to claim 6 wherein the caustic solution is maintained at a temperature of about 200° F.

8. A process according to claim 6 wherein the acyl isethionate salt is added to the reactor together in admixture with said fatty monocarboxylic acid.

9. A process according to claim 6 wherein the aqueous caustic solution contains from about 0.4 to about 2% of an electrolyte.

10. A process according to claim 6 wherein the aqueous caustic solution contains from about 0.8 to about 1.5% of an electrolyte.

11. A process according to claim 6 wherein said first feed stream is introduced at a point upstream from where said caustic solution enters said mixing chamber.

12. A process according to claim 6 wherein said acyl isethionate salt is fed into said mixing chamber at a point downstream both from said entry points of said caustic solution and said fatty monocarboxylic acid streams.

13. A process according to claim 6 wherein said mixing chamber is an extruder.

14. A process according to claim 1 wherein the high speed mixing under step (ii) is conducted at a temperature from at least 180° F. to about 200° F.

15. A process according to claim 14 wherein the high speed mixing under step (ii) is conducted at a temperature to about 200° F.

16. A process according to claim 1 further comprising including an alkali metal isethionate in an amount from about 3.1 to about 3.9% to the aqueous caustic solution of step (i).

17. A process according to claim 6 further comprising including an alkali metal isethionate in an amount from about 3.1 to about 3.9% to the aqueous caustic solution of step (i).

18. A process for the production of a composition comprising alkali metal salts of $C_8$–$C_{22}$ alkyl fatty monocarboxylic acid and $C_8$–$C_{22}$ acyl isethionate in a ratio of 20:1 to 1:0.98, said process comprising the steps of:
  (i) forming an aqueous caustic solution comprising sodium hydroxide in an amount sufficient to neutralize a $C_8$–$C_{22}$ alkyl fatty monocarboxylic acid and from 0 to 20% by weight of an alkali metal isethionate, said solution being maintained at a temperature from at least 180° F. to about 200°F. to obtain a hot solution;
  (ii) charging said $C_8$–$C_{22}$ alkyl fatty monocarboxylic acid to a reactor and agitating said fatty monocarboxylic acid under high speed mixing;
  (iii) slowly adding said hot caustic solution to said fatty monocarboxylic acid in said reactor; and
  (iv) feeding said acyl isethionate salt to said reactor at a time subsequent to the addition of said caustic solution in step (iii).

19. Process for continuous production of a composition comprising alkali metal salts of $C_8$–$C_{22}$ alkyl fatty acid and $C_8$–$C_{22}$ acyl isethionate in a ratio of about 20:1 to 1:0.98, said process comprising the steps of:
  (i) forming an aqueous caustic solution comprising sodium hydroxide in an amount sufficient to neutralize a $C_8$–$C_{22}$ alkyl fatty monocarboxylic acid and from 0 to 20% by weight of an alkali metal isethionate, said solution being maintained at a temperature from at least 180° F. to about 200° F. to obtain a hot solution;
  (ii) separately and simultaneously charging a first feed stream of said $C_8$–$C_{22}$ alkyl fatty monocarboxylic acid and a second feed stream of said hot caustic solution into a mixing chamber to form said alkali metal $C_8$–$C_{22}$ alkyl fatty monocarboxylic acid salt; and
  (iii) mixing said formed alkali metal $C_8$–$C_{22}$ alkyl fatty monocarboxylic acid salt with said alkali metal $C_8$–$C_{22}$ acyl isethionate salt to form said composition, and wherein said acyl isethionate salt is introduced subsequent to step (ii).

20. A process according to claim 1 wherein said alkali metal isethionate is present in said caustic solution in an amount from 0.5 to 10% by weight.

21. A processing according to claim 6 wherein said alkali metal isethionate is present in said caustic solution in an amount from 0.5 to 10% by weight.

22. A process according to claim 1 wherein said sodium hydroxide is present in an amount from 10 to 80% by weight of said caustic solution.

23. A process according to claim 6 wherein said sodium hydroxide is present in an amount from 10 to 80% by weight of said caustic solution.

24. A process according to claim 18 wherein the caustic solution is maintained at a temperature of about 200° F.

25. A process according to claim 18 wherein the acyl isethionate salt is added to the reactor together in admixture with said fatty monocarboxylic acid.

26. A process according to claim 18 wherein the aqueous caustic solution contains from about 0.4 to about 2% of an electrolyte.

27. A process according to claim 18 wherein the aqueous caustic solution contains from about 0.8 to about 1.5% of an electrolyte.

28. A process according to claim 19 wherein the caustic solution is maintained at a temperature of about 200° F.

29. A process according to claim 19 wherein the aqueous caustic solution contains from about 0.4 to about 2% of an electrolyte.

30. A process according to claim 19 wherein the aqueous caustic solution contains from about 0.8 to about 1.5% of an electrolyte.

31. A process according to claim 19 wherein the first feed stream is introduced at a point upstream from where said caustic solution enters said mixing chamber.

32. A process according to claim 19 wherein said acyl isethionate salt is fed into mixing chamber reactor at a point downstream both from said entry points of said caustic solution and said fatty monocarboxylic acid streams.

33. A process according to claim 19 wherein said mixing chamber is an extruder.

* * * * *